US010294463B2

(12) United States Patent
Castelli et al.

(10) Patent No.: US 10,294,463 B2
(45) Date of Patent: May 21, 2019

(54) **MODIFIED *BACILLUS CEREUS* PHOSPHOLIPASE C PROTEIN AND METHOD OF PROCESSING VEGETABLE OIL**

(71) Applicant: Keclon SA, Buenos Aires (AR)

(72) Inventors: Maria Eugenia Castelli, Rosario (AR); Hugo Menzella, Rosario (AR); Salvador Peiru, Rosario (AR); Leandro Vetcher, Cambridge, MA (US)

( * ) Notice: Subject to any disclaimer, the term of this patent is extended or adjusted under 35 U.S.C. 154(b) by 161 days.

(21) Appl. No.: 14/902,448

(22) PCT Filed: Jun. 19, 2014

(86) PCT No.: PCT/US2014/043294
§ 371 (c)(1),
(2) Date: Dec. 31, 2015

(87) PCT Pub. No.: WO2015/017045
PCT Pub. Date: Feb. 5, 2015

(65) Prior Publication Data
US 2017/0015981 A1     Jan. 19, 2017

Related U.S. Application Data

(60) Provisional application No. 61/842,880, filed on Jul. 3, 2013.

(51) Int. Cl.
*C12P 7/64* (2006.01)
*C12N 9/16* (2006.01)
*C11B 3/00* (2006.01)
*C12N 15/81* (2006.01)

(52) U.S. Cl.
CPC ............. *C12N 9/16* (2013.01); *C11B 3/003* (2013.01); *C12N 15/815* (2013.01); *C12P 7/6445* (2013.01); *C12Y 301/04003* (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 5,264,367 A | 11/1993 | Aalrust et al. | |
| 5,558,781 A | 9/1996 | Buchold et al. | |
| 6,001,640 A | 12/1999 | Loeffler et al. | |
| 6,103,505 A | 8/2000 | Clausen et al. | |
| 6,162,623 A | 12/2000 | Grote et al. | |
| 6,355,693 B1 | 3/2002 | Herslof et al. | |
| 7,226,771 B2 * | 6/2007 | Gramatikova | C12N 9/16 435/197 |
| 7,314,974 B2 * | 1/2008 | Cao | C07K 14/195 800/288 |
| 7,943,360 B2 * | 5/2011 | Gramatikova | C12N 9/16 435/18 |
| 8,298,799 B2 * | 10/2012 | Bornscheuer | A23C 9/20 435/195 |
| 9,024,113 B2 * | 5/2015 | Cao | C07K 14/195 435/320.1 |

OTHER PUBLICATIONS

Smith & Waterman, Comparison of Biosequences, Advances in Applied Mathematics 2, 482-489 (1981).
Hirschberg, et al, Cloning, expression, purification and characterization of patatin, a novel phospholipase A, Eur. J. Biochem. 268, 5037-5044 (2001).
Altschul, et al, Basic Local Alignment Search Tool, J. Mol. Biol. (1990) 215, 403-410.
Altschul, et al, Gapped BLAST and PSI-BLAST: a new generation of protein database search programs, Nucleic Acids Research, 1997, vol. 25, No. 17 3389-3402.
Pearson and Lipman, Improved tools for biological sequence comparison, Proc. Natl. Acad. Sci. USA vol. 85, pp. 2244-2448, Apr. 1988 Biochemistry.
Dobeli, Recombinant Fusion Proteins for the Industrial Production of Disulfide Bridge Containing Peptides: Purification, Oxidation without Concatamer Formation, and Selective Cleavage, Protein Expression and Purification 12, 404-414 (1998).

* cited by examiner

*Primary Examiner* — Hope A Robinson
(74) *Attorney, Agent, or Firm* — Eugenio J. Torres-Oyola; Victor M. Rodriguez-Reyes; Ferraiuoli LLC

(57) ABSTRACT

A modified *Bacillus cereus* phospholipase C enzyme is provided, as well as a method of using the modified phospholipase C enzyme in a method of treating vegetable oil. In certain embodiments, this method may comprise combining a vegetable oil with an modified phospholipase C enzyme comprising an amino acid sequence that is at least 85% identical to the amino acid sequence of SEQ ID NO:1, wherein the amino acid residue at position 66 is a Trp (W) or Tyr (Y), and maintaining the combination under conditions suitable for the modified phospholipase C enzyme to catalyze the hydrolysis of phospholipids in the oil to produce diacylglycerol and a water soluble phosphate.

Figure 1:
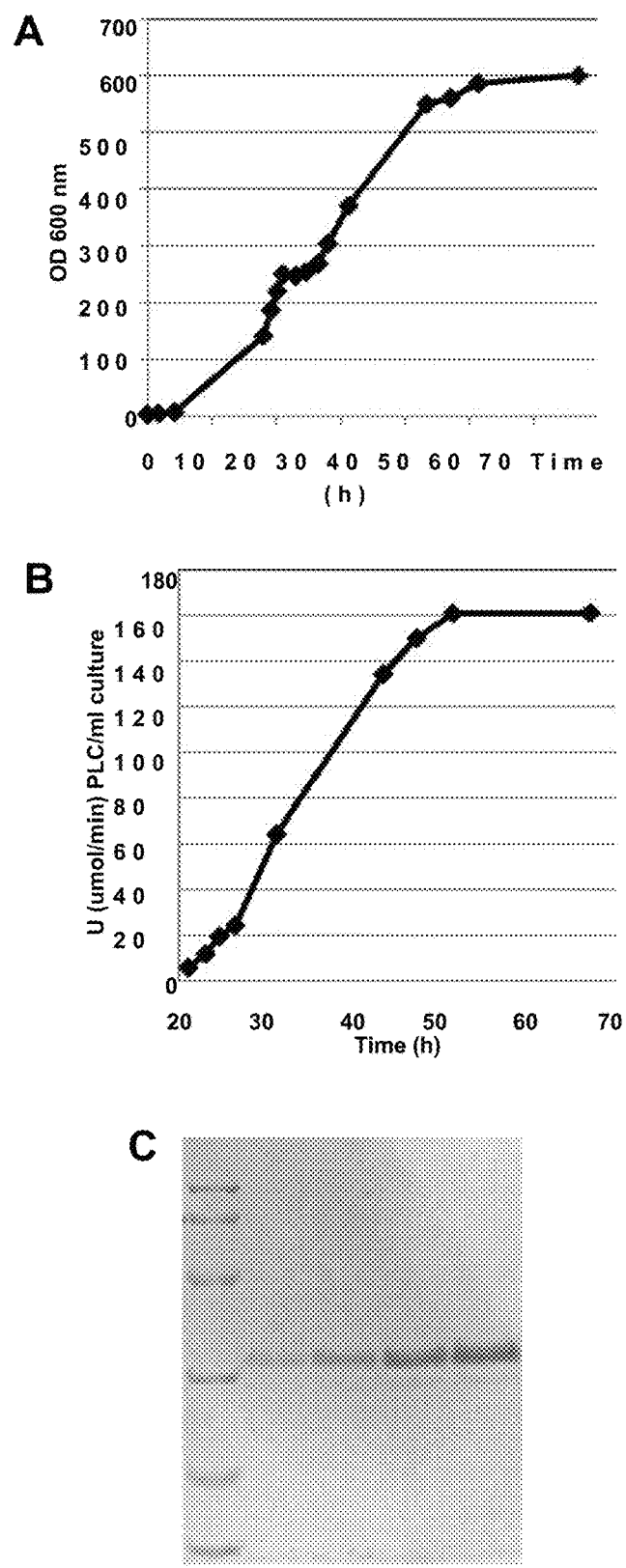

15 Claims, 3 Drawing Sheets
Specification includes a Sequence Listing.

| | ³¹P CHEMICAL SHIFTS (ppm) |
|---|---|
| PHOSPHOETHANOLAMINE | 3,82 |
| PHOSPHATIDIC ACID | 3,708 |
| PHOSPHOCHOLINE | 3,25 |
| PHOSPHATIDYLETHANOLAMINE | -0,1825 |
| PHOSPHATIDYLINOSITOL | -0,6555 |
| PHOSPHATIDYLCHOLINE | -0,809 |

SEQUENCE LISTING

```
<160> NUMBER OF SEQ ID NOS: 7

<210> SEQ ID NO 1
<211> LENGTH: 245
<212> TYPE: PRT
<213> ORGANISM: Bacillus cereus

<400> SEQUENCE: 1

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Leu Leu Asn Glu Trp Arg Thr Glu Leu Glu
        35                  40                  45

Asn Gly Ile Tyr Ala Ala Asp Tyr Glu Asn Pro Tyr Tyr Asp Asn Ser
    50                  55                  60

Thr Phe Ala Ser His Phe Tyr Asp Pro Asp Asn Gly Lys Thr Tyr Ile
65                  70                  75                  80

Pro Tyr Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Asp Trp Ile
                165                 170                 175

His Gly Ala Ala Val Val Ala Lys Gln Asp Tyr Ala Gly Ile Val Asn
            180                 185                 190

Asp Asn Thr Lys Asp Trp Phe Val Arg Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asn Arg
                245

<210> SEQ ID NO 2
<211> LENGTH: 738
<212> TYPE: DNA
<213> ORGANISM: Artificial sequence
<220> FEATURE:
<223> OTHER INFORMATION: Synthetic polynucleotide

<400> SEQUENCE: 2
tggtccgcag aagacaaaca taaggaaggt gtgaatagcc atttgtggat tgtgaaccgt      60
gccattgaca tcatgtcccg taataccacc ctggttaaac aagatcgcgt ggccctgtta     120
```

```
aatgaatggc gtactgaatt agaaaacggt atctatgctg cagattacga aaatccatat    180
tacgatgact ctacctgggc gtcacatttc tatgatccag acaacggcaa acatatatc    240 ccgtacgcta acaagcaaa ggaaacgggt gctaaatatt ttaagctggc aggcgaatcc    300
tacaagaata aggatatgaa gcaagcattt ttctatctgg gtctgtcgtt acattactta    360
ggcgatgtca accaacctat gcacgccgcg agcttcactg acttgagtta tccacagggt    420
ttccattcaa agtacgaaaa cttcgtcgat acaattaaag acaactacaa agtaacggat    480
ggtaatggct actggaactg gaagggtaca atccggaag attggattca cggcgctgca    540
gttgtggcca acaagacta tgcgggtatc gttaatgata cacgaagga ctggtttgtc    600 agagccgctg tttctcagga atcgctgat aaatggcgcg cagaagttac ccctatgact    660
ggcaagcgtt tgatggatgc ccaaagagtg accgcgggtt atatccagct gtggtttgac    720
acttacggca accgttaa                                                   738

<210> SEQ ID NO 3
<211> LENGTH: 245
<212> TYPE: PRT
<213> ORGANISM: Artificial sequence
<220> FEATURE:
<223> OTHER INFORMATION: Engineered PLC

<400> SEQUENCE: 3

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Leu Leu Asn Glu Trp Arg Thr Glu Leu Glu
        35                  40                  45

Asn Gly Ile Tyr Ala Ala Asp Tyr Glu Asn Pro Tyr Tyr Asp Asp Ser
    50                  55                  60

Thr Trp Ala Ser His Phe Tyr Asp Pro Asp Asn Gly Lys Thr Tyr Ile
65                  70                  75                  80

Pro Tyr Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Asp Trp Ile
                165                 170                 175

His Gly Ala Ala Val Val Ala Lys Gln Asp Tyr Ala Gly Ile Val Asn
            180                 185                 190

Asp Asn Thr Lys Asp Trp Phe Val Arg Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asn Arg
                245
```

<210> SEQ ID NO 4
<211> LENGTH: 738
<212> TYPE: DNA
<213> ORGANISM: Artificial sequence
<220> FEATURE:
<223> OTHER INFORMATION: Synthetic polynucleotide

<400> SEQUENCE: 4

```
tggtccgcag aagacaaaca taaggaaggt gtgaatagcc atttgtggat tgtgaaccgt      60
gccattgaca tcatgtcccg taataccacc ctggttaaac aagatcgcgt ggccctgtta     120
aatgaatggc gtactgaatt agaaaacggt atctatgctg cagattacga aaatccatat     180
tacgatgact ctacctacgc gtcacatttc tatgatccag acaacggcaa acatatatc     240
ccgtacgcta acaagcaaa ggaaacgggt gctaaatatt ttaagctggc aggcgaatcc     300
tacaagaata aggatatgaa gcaagcattt ttctatctgg gtctgtcgtt acattactta     360
ggcgatgtca accaacctat gcacgccgcg agcttcactg acttgagtta tccacagggt     420
ttccattcaa agtacgaaaa cttcgtcgat acaattaaag acaactacaa agtaacggat     480
ggtaatggct actggaactg gaagggtaca aatccggaag attggattca cggcgctgca     540
gttgtggcca aacaagacta tgcgggtatc gttaatgata acacgaagga ctggtttgtc     600
agagccgctg tttctcagga atacgctgat aaatggcgcg cagaagttac ccctatgact     660
ggcaagcgtt tgatggatgc ccaaagagtg accgcgggtt atatccagct gtggtttgac     720
acttacggca accgttaa                                                   738
```

<210> SEQ ID NO 5
<211> LENGTH: 245
<212> TYPE: PRT
<213> ORGANISM: Artificial sequence
<220> FEATURE:
<223> OTHER INFORMATION: Engineered PLC

<400> SEQUENCE: 5

```
Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
                20                  25                  30

Lys Gln Asp Arg Val Ala Leu Leu Asn Glu Trp Arg Thr Glu Leu Glu
            35                  40                  45

Asn Gly Ile Tyr Ala Ala Asp Tyr Glu Asn Pro Tyr Tyr Asp Asp Ser
        50                  55                  60

Thr Tyr Ala Ser His Phe Tyr Asp Pro Asp Asn Gly Lys Thr Tyr Ile
65                  70                  75                  80

Pro Tyr Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Asp Trp Ile
                165                 170                 175
```

His Gly Ala Ala Val Val Ala Lys Gln Asp Tyr Ala Gly Ile Val Asn
            180                 185                 190

Asp Asn Thr Lys Asp Trp Phe Val Arg Ala Ala Val Ser Gln Glu Tyr
            195                 200                 205

Ala Asp Lys Trp Arg Ala Glu Val Thr Pro Met Thr Gly Lys Arg Leu
210                 215                 220

Met Asp Ala Gln Arg Val Thr Ala Gly Tyr Ile Gln Leu Trp Phe Asp
225                 230                 235                 240

Thr Tyr Gly Asn Arg
                245

<210> SEQ ID NO 6
<211> LENGTH: 245
<212> TYPE: PRT
<213> ORGANISM: Artificial sequence
<220> FEATURE:
<223> OTHER INFORMATION: Engineered PLC

<400> SEQUENCE: 6

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Leu Leu Asn Glu Trp Arg Thr Glu Leu Glu
        35                  40                  45

Asn Gly Ile Tyr Ala Ala Asp Tyr Glu Asn Pro Tyr Tyr Asp Asp Ser
    50                  55                  60

Thr Phe Ala Ser His Phe Tyr Asp Pro Asp Asn Gly Lys Thr Tyr Ile
65                  70                  75                  80

Pro Tyr Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Asp Trp Ile
                165                 170                 175

His Gly Ala Ala Val Val Ala Lys Gln Asp Tyr Ala Gly Ile Val Asn
            180                 185                 190

Asp Asn Thr Lys Asp Trp Phe Val Arg Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asn Arg
                245

<210> SEQ ID NO 7
<211> LENGTH: 20
<212> TYPE: PRT
<213> ORGANISM: Bacillus cereus

```
<400> SEQUENCE: 7

Glu Asn Pro Tyr Tyr Asp Asn Ser Thr Phe Ala Ser His Phe Tyr Asp
1               5                   10                  15

Pro Asp Asn Gly
            20
```

MODIFIED BACILLUS CEREUS PHOSPHOLIPASE C PROTEIN AND METHOD OF PROCESSING VEGETABLE OIL

CROSS-REFERENCE TO RELATED APPLICATIONS

This application claims the benefit of International Application No. PCT/US2014/043294, filed Jun. 19, 2014, which claim priority to U.S. Provisional Application No. 61/842,880, filed on Jul. 3, 2013, which application is incorporated herein in its entirety.

BACKGROUND OF THE INVENTION

Phospholipase C catalyzes the hydrolysis of the sn-3 phosphate head group in phospholipids including phosphatidylcholine, phosphatidyletanolamine, and phosphatidylserine, resulting in the formation of 1,2-diacylglycerol and water soluble phosphate esters (e.g., phosphorylcholine, phosphorylethanolamine, and phosphorylserine). Because of this activity phospholipase C can be used for refining vegetable oils such as soybean oil.

Phospholipase C can be used to process vegetable oils, e.g., vegetable oils intended for human consumption or biodiesel production such as soybean, corn, canola, rapeseed, and sunflower oil. In many cases, degumming is the first step in the refining of crude oil. In enzymatic degumming, phospholipase C is added to crude oil, and the mixture is heated in the presence of water. Under these conditions, phospholipase C hydrolyses the major oil phospholipids, e.g., phosphatidylcholine and phosphatidylethanolamine. The resulting esters, e.g., phosphorylcholine and phosphorylethanolamine, are soluble in water and separated from the oil, e.g., by centrifugation. 1,2-diacylglycerol, which is also formed during the hydrolysis, remains in the oil phase. The residual phospholipase C can be removed from the oil during subsequent purification steps, e.g., by repeatedly washing of the oil with hot water, bleaching, and deodorization.

SUMMARY OF THE INVENTION

A modified *Bacillus cereus* phospholipase C polypeptide is provided, as well as a method of using the polypeptide in a method of treating vegetable oil. In certain embodiments, this method may comprise combining a vegetable oil with an isolated phospholipase C enzyme comprising an amino acid sequence that is at least 85% identical to the amino acid sequence of SEQ ID NO:1, wherein the amino acid residue at position 66 is a Trp (W) or Tyr (Y), and maintaining the combination under conditions suitable for the phospholipase C enzyme to catalyze the hydrolysis of phospholipids in the oil.

BRIEF DESCRIPTION OF THE DRAWINGS

Various figures are provided herewith. The skilled artisan will understand that the drawings, described below, are for illustration purposes only. The drawings are not intended to limit the scope of the present teachings in any way.

FIG. 1 shows graphs of *Pichia pastoris* fermentation. 1A. Growth curve. 1B. Phospholipase C activity measured with O-(4-nitrophenylphosphoryl) choline as substrate. 1C. SDS-PAGE analysis of supernatant. Samples were taken at 21, 30, 45 and 65 h.

FIG. 2 shows a graph of phospholipase C activity of $PLC_{BC}$, $PLC_{BCW}$ and $PLC_{BCY}$ in aqueous media with O-(4-nitrophenylphosphoryl) choline. Phospholipase C activity of $PLC_{BC}$, $PLC_{BCW}$ and $PLC_{BCY}$ were compared using 2.2 μM protein and 1 m MO-(4-nitrophenylphosphoryl) choline. OD 405 nm was monitored for 1 h at 55° C.

FIG. 3 shows a graph of oil degumming by $PLC_{BC}$, $PLC_{BCW}$ and $PLC_{BCY}$ Phospholipase C activity in crude soybean oil of $PLC_{BC}$, $PLC_{BCW}$ and $PLC_{BCY}$ were compared using 2.2 μM protein as described in the materials and methods section.

FIG. 4. NMR analysis of crude and $PLC_{BCY}$ treated oil. Crude soybean oil was treated with $PLC_{BCY}$ for 2 hs at 55° C. Treated oil was extracted as described in methods and analyzed by NMR.

DEFINITIONS

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "contacting" means to bring or put together. As such, a first item is contacted with a second item when the two items are brought or put together, e.g., by touching them to each other or combining them in the same solution.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

The term "construct" refers to any polynucleotide that contains a recombinant nucleic acid. A construct may be present in a vector (e.g., a viral vector) or may be integrated in a genome, for example.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or 'transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, "expression vector" refers to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid," "expression plasmid," and "vector" are often used interchangeably as the plasmid is the most commonly used form of vector at present. However, the invention is intended to include such other forms of expression vectors that serve equivalent functions and which are, or become, known in the art.

As used herein, "corresponding to," refers to a residue at the enumerated position in a protein or peptide, or a residue that is equivalent in position to the enumerated residue in a different protein or peptide. Identifying corresponding amino acids may be done by aligning the sequences and identifying residues that like across from one another in the resultant alignment. In other words, the residue number or residue position of a given polymer is designated with respect to the reference sequence rather than by the actual numerical position of that residue within the given amino acid or polynucleotide sequence.

As used herein, "wild-type", "native" and "naturally-occurring" refers to proteins are those found in nature. The term "wild-type sequence," is used herein to refer to a sequence that is native or naturally occurring in a host cell. The term "non-naturally occurring" refers to proteins that are not found in nature.

As used herein, the term "isolated" refers to a substance that has been removed from the source in which it naturally occurs. A substance need not be purified in order to be isolated. For example, a protein produced in a host cell is considered isolated when it is removed or released from the cell. A protein contained within a crude cell lysate fraction is considered "isolated" for purposes of the present disclosure.

As used herein, the term "purified" refers to a substance that has been rendered at least partially free of contaminants and other materials that typically accompany it. Substances can be purified to varying degrees. A substance is "substantially pure" when a preparation or composition of the substance contains less than about 1% contaminants. A substance is "essentially pure" when a preparation or composition of the substance contains less than about 5% contaminants. A substance is "pure" when a preparation or composition of the substance contains less than about 2% contaminants. For substances that are "purified to homogeneity," contaminants cannot be detected with conventional analytical methods. The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

The term "heterologous" refers to elements that are not normally associated with each other. For example, if a host cell produces a heterologous protein, that protein that is not normally produced in that host cell. Likewise, a promoter that is operably linked to a heterologous coding sequence is a promoter that is operably linked to a coding sequence that it is not usually operably linked to in a wild-type host cell. The term "homologous", with reference to a polynucleotide or protein, refers to a polynucleotide or protein that occurs naturally in a host cell.

As used herein, the terms "percent sequence identity," "percent identity," and/or "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence in order to effect optimal alignment. The percentage identity is calculated by dividing the number of matched portions in the comparison window by the total number of positions in the comparison window, and multiplying by 100. The number of matched positions in the comparison window is the sum of the number of positions of the comparison polynucleotide or polypeptide in the window that are identical in sequence to the reference polynucleotide or polypeptide and the number of positions of the reference polynucleotide or polypeptide in the comparison window that align with a gap in the comparison polynucleotide or polypeptide. Determination of optimal alignment and percent sequence identity is performed using the BLAST and BLAST 2.0 algorithms (see, e.g., Altschul et al., 1990, J. Mol. Biol. 215:403-410 and Altschul et al., 1997, Nucleic Acids Res. 25(17):3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, 1990, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penaltyscore for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989, Proc. Nat'l Acad. Sci. USA 89:10915). Numerous other algorithms are available that function similarly to BLAST in providing percentage identity between sequences.

Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., 1995 Supplement).

As used herein, the term "reference sequence" refers to a specified sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered, variant and/or altered sequences.

As used herein, the term "comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, the term "amino acid substitution" refers to the replacement of a first amino acid with any other amino acid.

A "conservative" amino acid substitution is a substitution of an amino acid from the same group, where the groups are defined as follows: group 1: gly, ala; group 2: val, ile, leu; group 3: asp, glu; group 4: asn, gln; group 5: ser, thr; group 6: lys, arg; and group 7: phe, tyr.

The term "phospholipase" refers an enzyme having any phospholipase activity, for example, cleaving a glycerolphosphate ester linkage (catalyzing hydrolysis of a glycerolphosphate ester linkage), e.g., in an oil, such as a vegetable oil. A phospholipase activity can generate a water extractable phosphorylated base and a diglyceride. A phospholipase activity also includes hydrolysis of glycerolphosphate ester linkages at high temperatures, low temperatures, alkaline pHs and at acidic pHs. The term "a phospholipase activity" also includes cleaving a glycerolphosphate ester to generate a water extractable phosphorylated base and a diglyceride. The term "a phospholipase activity" also includes cutting ester bonds of glycerin and phosphoric acid in phospholipids. The phospholipase activity can comprise a phospholipase C (PLC) activity; a phospholipase A (PLA) activity, such as a phospholipase A1 or phospholipase A2 activity; a phospholipase B (PLB) activity, including lysophospholipase (LPL) activity and/or lysophospholipase-transacylase (LPTA) activity; a phospholipase D (PLD) activity; and/or a patatin activity or any combination thereof. An enzyme that has phospholipase activity may have other catalytic activities in addition to a phospholipase activity.

The term "vegetable oil" refers to any oil that can be processed from a vegetable, particularly an oil that can be processed for human or animal consumption such as rice bran oil, palm oil, rapeseed oil, corn oil, soybean oil, canola oil, sesame oil, peanut oil or sunflower oil. This term includes raw oil as well as partially processed versions of the same.

For clarity and unless otherwise indicated, all enumerated amino acid positions in this disclosure are with reference to the following PLC sequence (from *Bacillus cereus*; the secreted form of the protein of Genbank Accession No. GI:218233076): WSAEDKHKEGVNSHLWIVNRAIDIM-SRNTTLVKQDRVALLNEWRTELENGIYAADYENP YYDNSTFASHFYDPDNGKTYIPYAKQAKETGAKY-FKLAGESYKNKDMKQAFFYLGLSL HYLGDVNQPM-HAANFTNLSYPQGFHSKYENFVDTIKDNYKVT-DGNGYWNWKGTNPED WIHGAAVVAKQDYAGIVNDNTKDWFVRAAVSQEY-ADKWRAEVTPMTGKRLMDAQRV TAGYIQLWFD-TYGNR(SEQ ID NO:1). If a protein is indicated as having a substitution, the protein has a substitution at the position that corresponds to the indicated position. For example, if a protein is described as having the following amino acid substitutions F66W or F66Y or "wherein the amino acid residue at position 66 is a Trp (W) or a Tyr (Y)", the protein will have a tryptophan residue or a tyrosine residue at the position that corresponds to position 66 in SEQ ID NO:1.

Other definitions of terms may appear throughout the specification.

DESCRIPTION OF EXEMPLARY EMBODIMENTS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

A method for treating a vegetable oil is provided. In certain embodiments, this method may comprise combining vegetable oil with an isolated phospholipase C enzyme comprising an amino acid sequence that is at least 85% identical (e.g., at least 90% identical, at least 95% identical, at least 98% identical, at least 99% or 100% identical) to the amino acid sequence of SEQ ID NO:1, except that the amino acid residue at position 66 (underlined in the following sequence ENPYYDNSTFASHFYDPDNG (SEQ ID NO:7)) is a Trp (W) or Tyr (Y). Optionally, the amino acid residues at positions 63, 131 and 134 are not Asn (N). For example, in one embodiment, the amino acid residues at positions 63 is an Asp (D), the amino acid residue at position 131 is a Ser (S) and the amino acid residue at position 134 is an Asp (D). The resultant combination is maintained under conditions suitable for the phospholipase C activity of the enzyme to catalyze the hydrolysis of phospholipids in the oil to produce a water soluble phosphate ester. Depending on whether other enzymes are included, the reaction may also produce diacylglycerol, monoacylglycerol or glycerol. In many cases, the reaction results in 1,2-diacylglycerol and a water soluble phosphate ester. The vegetable oil can be from any suitable plant, including soybeans, rapeseed, sunflower seeds, rice bran oil, sesame or peanuts, for example. In some cases (and depending on the oil and other enzymes used), phosphati-dylcholine and/or phosphatidylethanolamine may be hydrolyzed to produce diacylglycerol and water-soluble phosphate esters of choline and ethanolamine, respectively.

In some cases, the method may comprise contacting the vegetable oil with the phospholipase C enzyme, and incubating the mixture to a temperature of at least 40° C. in the optional presence of, e.g., 0.5%-5% (v/v) water. In some embodiments, the method may further comprise separating the water soluble phosphate esters from the diacylglycerol. This may be done by centrifugation, although other separation methods may be used.

In particular embodiments, the polypeptide may be combined with the vegetable oil at a ratio in the range of 100 to 1000 grams (e.g., 200 to 800 grams) grams of protein per metric ton of oil.

Also provided herein is a composition of matter comprising a vegetable oil and an isolated phospholipase C enzyme comprising the amino acid sequence that is at least 85% identical (e.g., at least 90% identical, at least 95% identical, at least 98% identical, at least 99% or 100% identical) to the amino acid sequence of SEQ ID NO:1, wherein: the amino acid residue at position 66 is a Trp (W) or Tyr (Y). Optionally, the amino acid residues at positions 63, 131 and 134 are not Asn (N), e.g., the amino acid residues at positions 63 is an Asp (D), the amino acid residue at position 131 is a Ser (S) and the amino acid residue at position 134 is an Asp (D), as described above. In certain embodiments, the vegetable is oil from soybeans, rapeseed, sunflower seeds, rice bran oil, sesame or peanuts, for example. In certain cases, the composition comprises up to 10% water v/v, e.g., (up to 5% water, up to 4% water, up to 3% water, up to 2% water or up to 1% water or less than 0.05% water) and may be at an elevated temperature, e.g., a temperature of at least 40° C., e.g., a temperature in the range of 45° C. to 80° C. In particular embodiments, the protein may be thermotolerant in that it, e.g., retains at least 90% of its phospholipase activity when its temperature is raised from 37° C. to a selected temperature in the range of 45° C. to 80° C. Also provided herein is an isolated phospholipase C enzyme comprising the amino acid sequence that is at least 85% identical to the amino acid sequence of SEQ ID NO:1, wherein: the amino acid residue at position 66 is a Trp (W) or Tyr (Y) and the amino acid residues at positions 63, 131 and 134 are not Asn (N). In some embodiments, the amino acid residues at positions 63, 131 and 134 are independently selected from a Ser (S) and an Asp (D). For example, in one embodiment, the amino acid residues at positions 63 is an Asp (D), the amino acid residue at position 131 is a Ser (S) and the amino acid residue at position 134 is an Asp (D). In particular embodiments, the amino acid sequence of the isolated polypeptide comprises the amino acid sequence of SEQ ID NO:3 or SEQ ID NO:5. In any embodiment, the amino acid residue at position 134 of the isolated phospholipase Cenzyme is an Ala (A).

In any embodiment, the isolated phospholipase C enzyme may have the amino acid sequence of SEQ ID NO: 5, with the exception of the following amino acid substitutions: Q139W, D63M, D63F or D63W.

In any embodiment, the isolated phospholipase C enzyme may have the amino acid sequence of SEQ ID NO: 5, with the exception of the following amino acid substitution: Y56T.

A nucleic acid encoding the isolated phospholipase C enzyme is also provided. In certain embodiments, the nucleotide sequence of the nucleic acid is set forth in SEQ ID NO:2, wherein the codon defined by positions 196-198 is a TGG or TAC. A cell comprising this nucleic acid is also provided. In certain cases, the cell is a *Pichia pastoris* cell and the nucleotide sequence of the nucleic acid is set forth in SEQ ID NO:2, wherein the codon defined by positions 196-198 is a TGG or TAC. Such a cell may be used to make the above-described polypeptide. In one embodiment, this method may comprise incubating cells containing the nucleic acid, and harvesting the phospholipase C from the culture medium.

Phospholipases are enzymes that hydrolyze the ester bonds of phospholipids. Several types of phospholipases are known which differ in their specificity according to the position of the bond attacked in the phospholipid molecule. Phospholipase A1 (PLA1) removes the 1-position fatty acid to produce free fatty acid and 1-lyso-2-acylphospholipid. Phospholipase A2 (PLA2) removes the 2-position fatty acid to produce free fatty acid and 1-acyl-2-lysophospholipid. PLA1 and PLA2 enzymes can be intra- or extra-cellular, membrane-bound or soluble. Intracellular PLA2 is found in almost every mammalian cell. Phospholipase C (PLC) removes the phosphate moiety to produce 1,2 diacylglycerol and phosphate ester. Phospholipase D (PLD) produces 1,2-diacylglycerophosphate and base group. PLC and PLD are important in cell function and signaling. PLD had been the dominant phospholipase in biocatalysis (see, e.g., Godfrey, T. and West S. (1996) Industrial enzymology, 299-300, Stockton Press, New York). Patatins are another type of phospholipase, thought to work as a PLA (see for example, Hirschberg H J, et al., (2001), Eur J Biochem 268(19):5037-44).

Common oilseeds, such as soybeans, rapeseed, sunflower seeds, rice bran oil, sesame and peanuts are used as sources of oils and feedstock. In the oil extraction process, the seeds are mechanically and thermally treated. The oil is separated and divided from the meal by a solvent. Using distillation, the solvent is then separated from the oil and the oil is recovered. The oil is "degummed" and refined. The solvent content in the meal can be evaporated by thermal treatment, followed by meal drying and cooling. After a solvent had been separated by distillation, the produced raw oil can be processed using special degumming procedures and physical refining. The oil can also be utilized as feedstock for the production of fatty acids and methyl ester. The meal can be used for animal food.

Degumming is usually the first step in vegetable oil refining and it is designed to remove contaminating phosphatides that are extracted with the oil but interfere with the subsequent oil processing. These phosphatides are soluble in the vegetable oil only in an anhydrous form and can be precipitated and removed if they are hydrated. Hydration may be accomplished by mixing a small proportion of water with substantially dry oil in the presence of phospholipase C enzyme. The temperature of the reaction is not highly critical, although separation of the hydrated gums is more efficient when the viscosity of the oil is reduced at 50° C. to 80° C.

Degumming is described in a variety of publications, including, e.g., Godfrey, T. and West S. (1996) Industrial Enzymology, pp. 299-300, Stockton Press, New York; Dahlke (1998) "An enzymatic process for the physical refining of seed oils," Chem. Eng. Technol. 21:278-281; Clausen (2001) "Enzymatic oil degumming by a novel microbial phospholipase," Eur. J. Lipid Sci. Technol. 103: 333-340; Antikainen et al, which are incorporated by reference herein.

The nucleic acid and protein described herein may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems. In some embodiments, the nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

In one aspect, a nucleic acid encoding a subject phospholipase C enzyme is assembled in appropriate phase with a leader sequence capable of directing secretion of the translated polypeptide or fragment thereof.

In certain embodiments, the polypeptide can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

A nucleic acid may be operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the *E. coli* lac or trp promoters, the lad promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Expression vectors are encoding a subject polypeptide are also provided. Expression vectors can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *Bacillus, Pichia, Aspergillus* and yeast, etc). Vectors include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

An expression vector may comprise a promoter, a ribosome-binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolatereductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

A DNA sequence may be inserted into a vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook.

Such procedures and others are deemed to be within the scope of those skilled in the art. Transformed cell comprising a nucleic acid encoding a subject polypeptide are also provided. The host cell may be any of the host cells familiar to those skilled in the art, including prokaryotic cells, eukaryotic cells, such as bacterial cells, fungal cells, yeast cells, mammalian cells, insect cells, or plant cells. Enzymes of the invention can be expressed in any host cell, e.g., any bacterial cell, any yeast cell, e.g., *Pichia pastoris, Saccharomyces cerevisiae* or *Schizosaccharomyces pombe*. Exemplary bacterial cells include *E. coli, Lactococcus lactis, Streptomyces coelicolor, Bacillus subtilis, Bacillus cereus, Salmonella typhimurium* or any species within the genera *Bacillus, Streptomyces* and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

The subject polypeptide can be used in various vegetable oil processing steps, such as in vegetable oil extraction, particularly, in the removal of phospholipid gums in a process called "oil degumming". These processes can be used in a process scale, e.g., on a scale from about 15,000; 25,000; 50,000; 75,000; or 100,000 or more lbs of refined oil/day up to about 1, 2, 3, 4, 5 or 6 or more million lbs refined oil/day.

In one embodiment, this disclosure provides processes comprising use of a subject, enzyme to reduce gum mass and increase neutral oil (triglyceride) gain through reduced oil entrapment. In one embodiment, the process comprises use of a subject polypeptide for increasing neutral oils and diacylglycerol (DAG) production to contribute to the oil phase. The degumming process may additionally comprise use of one or more other enzymes such as a protease, an amylase, a lipase, a cutinase, another phospholipase (including, e.g., an enzyme of the invention), a carbohydrase, a cellulase, a pectinase, a mannanase, an arabinase, a galactanase, a xylanase, an oxidase, e.g., a lactase, and/or a peroxidase, or polypeptides with equivalent activity, or a combination thereof.

The subject polypeptide can be used in various vegetable oil processing steps, such as in vegetable oil extraction, particularly, in the removal of "phospholipid gums" in a process called "oil degumming," as described above. The invention provides methods for processing vegetable oils from various sources, such as rice bran, soybeans, rapeseed, peanuts and other nuts, sesame, sunflower, palm and corn. The methods can used in conjunction with processes based on extraction with as hexane, with subsequent refining of the crude extracts to edible oils. The first step in the refining sequence is the so-called "degumming" process, which serves to separate phosphatides by the addition of water. The material precipitated by degumming is separated and further processed to mixtures of lecithins. The commercial lecithins, such as soybean lecithin and sunflower lecithin, are semi-solid or very viscous materials. They consist of a mixture of polar lipids, mainly phospholipids, and oil, mainly triglycerides.

The subject polypeptide can be used in any "degumming" procedure, including water degumming, ALCON oil degumming (e.g., for soybeans), safinco degumming, "super degumming," UF degumming, TOP degumming, uni-degumming, dry degumming and ENZYMAX™ degumming. See, e.g., U.S. Pat. Nos. 6,355,693; 6,162,623; 6,103,505; 6,001,640; 5,558,781; 5,264,367. Various "degumming" procedures incorporated by the methods of the invention are described in Bockisch, M. (1998) In Fats and Oils Handbook, The extraction of Vegetable Oils (Chapter 5), 345-445, AOCS Press, Champaign, Ill. The phospholipases of the invention can be used in the industrial application of enzymatic degumming of triglyceride oils as described, e.g., in EP 513 709.

In one aspect, subject polypeptide is used to treat vegetable oils, e.g., crude oils, such as rice bran, soy, canola, flower and the like. In one aspect, this improves the efficiency of the degumming process. In one aspect, the invention provides methods for enzymatic degumming under conditions of low water, e.g., in the range of between about 0.1% to 20% water, or, 0.5% to 10% water. In one aspect, this results in the improved separation of a heavy phase from the oil phase during centrifugation. The improved separation of these phases can result in more efficient removal of phospholipids from the oil, including both hydratable and nonhydratable oils. In one aspect, this can produce a gum fraction that contains less entrained neutral oil (triglycerides), thereby improving the overall yield of oil during the degumming process.

In one aspect, the method may comprise hydrolysis of hydrated phospholipids in oil at a temperature of about 20° C. to 40° C., at an alkaline pH, e.g., a pH of about pH 8 to pH 10, using a reaction time of about 10 minutes to 10 hours, e.g., 1 hr to 5 hr. This can result in less than 10 ppm final oil phosphorus levels. In certain cases, the method may comprise hydrolysis of hydratable and non-hydratable phospholipids in oil at a temperature of about 50° C. to 60° C., at a pH slightly below neutral, e.g., of about pH 5 to pH 6.5, using a reaction time of, 10 minutes to 10 hours, e.g., 1 hr to 5 hr. This can result in less than 10 ppm final oil phosphorus levels.

In one aspect, the subject polypeptide may be used to hydrolyze a glycerylphosphoester bond and thereby enable the return of the diacylglyceride portion of phospholipids back to the oil, e.g., a vegetable, fish or algae oil; and, reduce the phospholipid content in a degumming step to levels low enough for high phosphorus oils to be physically refined. The two approaches can generate different values and have different target applications.

In one exemplary process, when the enzyme is added to and reacted with a crude oil, the amount of phospholipase employed is about 10-10,000 units, or, alternatively, about, 100-2,000 units, per 1 kg of crude oil. The enzyme treatment may be conducted for 5 min to 10 hours at a temperature of 30° C. to 90° C., or, alternatively, about, 40° C. to 70° C. The conditions may vary depending on the optimum temperature of the enzyme. The amount of water added may be 0.1-20 wt. parts per 100 wt. parts of crude oil. In some cases, the final mixture may be composed of 1% to 10%, water, e.g., 2-4% water.

Upon completion of such enzyme treatment, the liquid may separated with an appropriate means such as a centrifugal separator and the processed oil is obtained. Phosphorus-containing compounds produced by enzyme decomposition of gummy substances in such a process are practically all transferred into the aqueous phase and removed from the oil phase. Upon completion of the enzyme treatment, if necessary, the processed oil can be additionally washed with water or organic or inorganic acid such as, e.g., acetic acid, citric acid, phosphoric acid, succinic acid, and equivalent acids, or with salt solutions.

In one exemplary process for ultra-filtration degumming, the enzyme is bound to a filter or the enzyme is added to an oil prior to filtration or the enzyme is used to periodically clean filters.

In one exemplary process for a phospholipase-mediated physical refining aid, water and enzyme are added to crude oil (e.g., crude vegetable oil). In one aspect, a subject polypeptide and a phosphatase are used in the process. In phospholipase-mediated physical refining, the water level can be low, i.e. 0.5-5% and the process time should be short (less than 2 hours, or, less than 60 minutes, or, less than 30 minutes, or, less than 15 minutes, or, less than 5 minutes). The process can be run at different temperatures (25° C. to 70° C.), using different acids and/or caustics, at different pHs (e.g., 3-10).

In alternate aspects, water degumming is performed first to collect lecithin by centrifugation and then a subject polypeptide is added to remove non-hydratable phospholipids (the process should be performed under low water concentration). In another aspect, water degumming of crude oil to less than 10 ppm (edible oils) and subsequent physical refining (less than 50 ppm for biodiesel) is performed. In one aspect, an emulsifier is added and/or the crude oil is subjected to an intense mixer to promote mixing. Alternatively, an emulsion-breaker is added and/or the crude oil is heated to promote separation of the aqueous phase. In another aspect, an acid is added to promote hydration of non-hydratable phospholipids. Additionally, phospholipases can be used to mediate purification of phytosterols from the gum/soapstock.

In certain cases, a subject polypeptide and at least one plant cell wall degrader (e.g., a cellulase, a hemicellulase or the like, to soften walls and increase yield at extraction) can be used. In this exemplary approach to using enzymes of the invention to improve oil extraction and oil degumming, subject polypeptide as well as other hydrolases (e.g., a cellulase, a hemicellulase, an esterase, a protease and/or a phosphatase) are used during the crushing steps associated with oil production (including but not limited to soybean, canola, sunflower, rice bran oil). By using enzymes prior to or in place of solvent extraction, it is possible to increase oil yield and reduce the amount of hydratable and non-hydratable phospholipids in the crude oil. The reduction in non-hydratable phospholipids may result from conversion of potentially non-hydratable phospholipids to diacylglycerol and corresponding phosphate-ester prior to complexation with calcium or magnesium. The overall reduction of phospholipids in the crude oil will result in improved yields during refining with the potential for eliminating the requirement for a separate degumming step prior to bleaching and deodorization.

In one aspect, to allow the enzyme of the invention to act, both phases, the oil phase and the aqueous phase that contain the enzyme, must be intimately mixed. It may not be sufficient to merely stir them. Good dispersion of the enzyme in the oil is aided if it is dissolved in a small amount of water, e.g., 0.5-5 weight-% (relative to the oil), and emulsified in the oil in this form, to form droplets of less than 10 micrometers in diameter (weight average). The droplets can be smaller than 1 micrometer. Turbulent stirring can be done with radial velocities above 100 cm/s. The oil also can be circulated in the reactor using an external rotary pump. The aqueous phase containing the enzyme can also be finely dispersed by means of ultrasound action. A dispersion apparatus can be used.

The enzymatic reaction may take place at the border surface between the oil phase and the aqueous phase and, as such, the addition of surfactants may increase the microdispersion of the aqueous phase. In some cases, therefore, surfactants with HLB values above 9, such as Na-dodecyl sulfate, are added to the enzyme solution, as described, e.g., in EP-A 0 513 709. A similar effective method for improving emulsification is the addition of lysolecithin. The amounts added can lie in the range of 0.001% to 1%, with reference to the oil. The temperature during enzyme treatment is not critical. Temperatures between 20° C. and 80° C., e.g., 30° C. and 50° C., can be used, but the latter can only be applied for a short time. The treatment period depends on the temperature and can be kept shorter with an increasing temperature. Times of 0.1 to 10 hours, or, 1 to 5 hours may be sufficient. In certain cases, the reaction may take place in a degumming reactor, which can be divided into stages, as described, e.g., in DE-A 43 39 556. Therefore continuous operation is possible, along with batch operation. The reaction can be carried out in different temperature stages. For example, incubation can take place for 3 hours at 40° C., then for 1 hour at 60° C. If the reaction proceeds in stages, this also opens up the possibility of adjusting different pH values in the individual stages. For example, in the first stage the pH of the solution can be adjusted to 7, for example, and in a second stage to 2.5, by adding citric acid. In at least one stage, however, the pH of the enzyme solution must be below 4, or, below 3. If the pH was subsequently adjusted below this level, a deterioration of effect may be found. Therefore the citric acid can be added to the enzyme solution before the latter is mixed into the oil.

After completion of the enzyme treatment, the enzyme solution, together with the decomposition products, can be separated from the oil phase, in batches or continuously, e.g., by means of centrifugation. Since the enzymes are characterized by a high level of stability and the amount of the decomposition products contained in the solution is slight (they may precipitate as sludge) the same aqueous enzyme phase can be used several times. There is also the possibility of freeing the enzyme of the sludge, see, e.g., DE-A 43 39 556, so that an enzyme solution which is essentially free of sludge can be used again. In one aspect of this degumming process, oils which contain less than 15 ppm phosphorus are obtained. One goal is phosphorus contents of less than 10 ppm; or, less than 5 ppm. With phosphorus contents below 10 ppm or below 5 ppm, further processing of the oil according to the process of distillative de-acidification is easily possible. A number of other ions, such as magnesium, calcium, zinc, as well as iron, can be removed from the oil, e.g., below 0.1 ppm. Thus, this product possesses ideal prerequisites for good oxidation resistance during further processing and storage. In certain cases, an oil degumming process may produce a product that contains 50-70 ppm phosphate.

EXAMPLES

The following examples are provided in order to demonstrate and further illustrate certain embodiments and aspects of the present invention and are not to be construed as limiting the scope thereof.

In the following description, $PLC_{BC}$ corresponds to protein SEQ ID NO:6, $PLC_{BCW}$ corresponds to SEQ ID NO:3 and $PLC_{BCY}$ corresponds to SEQ ID NO:5. SEQ ID NO:2 is codon optimized $PLC_{BCW}$ and SEQ ID NO:4 is codon optimized $PLC_{BCY}$.

Gene Design and Synthesis

Protein sequences were reverse translated and codon optimized using a codon randomization method (Menzella Microbial Cell Factories 2011 10:15). Briefly, the method consists on randomly assigning a triplet for each amino acid using a preference table for *Pichia pastoris* available at the kazusa.or.jp website, with a probability based on the weight of each codon within the set encoding a given amino acid. The designed genes were synthesized by Genescript (NJ, USA).

Plasmid and Strain Construction

The PLC codon optimized sequences were synthesized with XhoI-XbaI restriction sites at the borders and cloned into identical sites of the pJ912 vector (DNA2.0). The resulting plasmids were linearized with SacI and transformed by electroporation into *Pichia pastoris* cells. Transformants were selected on YPD supplemented with zeocin 100 μg/ml. 100 colonies were streaked on PLC activity plates (YP 5% egg yolk, 0.5% methanol, 1 mM ZnSO4, 1.5% agar) and colonies displaying the largest halos were selected for further analysis.

High Cell Density *Pichia pastoris* Fermentation

Fermentation of *Pichia pastoris* strain expressing the corresponding enzymes was performed according to the Invitrogen protocol for mut$^+$ strains. The culture medium used is 1 L of Fermentation Basal Salts Medium (BSM) pH 5 and cultures were grown at 30° C. in an Infors LabFors 4 bioreactor with 2 L of working volume.

The process starts with a 16 h batch phase followed by 3 hs of fed batch where the feeding rate is 18.12 ml/h·L of glycerol 50% WN+1.2% *Pichia* trace metals (PTM1). Next, a methanol feeding phase of 40 h induces the expression of the enzymes. The feeding rates (methanol 100%+1.2% PTM1) in the induction phase is 3.6 ml/h·L for the first 2 h, 7.6 ml/h·L for 2 additional hours and 10.9 ml/h·l until the end of the process. The typical process yield is 5 g/L of secreted protein, a final $OD_{660}$ of 600, and an overall PLC volumetric productivity of 3100 Units/L·h (FIG. 1A-C).

PLC Activity Using O-(4-Nitrophenylphosphoryl)choline Substrate

To determine PLC activity in the fermentation supernatant, 10 µl of 1/100 dilution of supernatant from *Pichia pastoris* cultures were incubated with 10 mM O-(4-Nitrophenylphosphoryl)choline as a substrate in buffer 250 mM HEPES pH7, 0.1 mM ZnCl2 in a final volume of 100 µl at 55° C. for 30 min. Absorbance at 405 nm determined and PLC activity calculated. 1 PLC unit corresponds to the amount of enzyme releasing 1 µmol of p-nitrophenol per minute.

Figure 2:
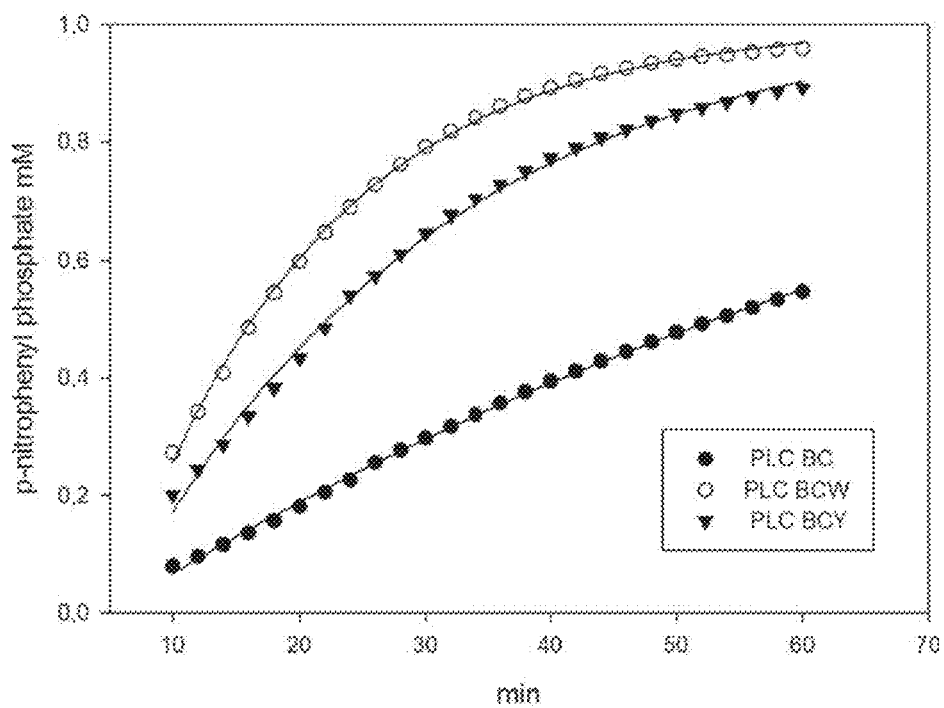

Kinetic Comparison of $PLC_{BC}$, $PLC_{BCW}$ and $PLC_{BCY}$ with O-(4-Nitrophenylphosphoryl)choline as a Substrate PLC activity was measured in 96 well microplates using 1 mM O-(4-Nitrophenylphosphoryl)choline as a substrate and 2.2 µM of each PLC in buffer 250 mM HEPES pH 7, 60% sorbitol, 0.1 mM ZnCl2. Absorbance at 405 nm was monitored for 1 h at 50° C. The obtained data were fitted to the integrated Michaelis-Menten rate equation to obtain the corresponding curves to determine $v_{max}/K_m$ (FIG. 2).

To determine $V_{max}$ and $K_m$, PLC activity was measured using an enzyme concentration of 1.2 µM. Different substrate solutions (50, 20, 10, 5, 2, 1, 0.5 and 0.1 mM) prepared in buffer 250 mM HEPES pH 7, 60% sorbitol, 0.1 mM ZnCl2 were used and absorbance at 405 nm was monitored for 1 h at 50° C. V0 was determined for each substrate concentration and $v_{max}$ and $K_m$ were estimated from a V0 vs [S] curve. As shown in Table 1, the mutant enzymes showed a significant increase in the $K_{cat}/K_m$ parameter, being the $PLC_{BCW}$ the enzyme with the best catalytic efficiency.

TABLE 1

Kinetic parameters of $PLC_{BC}$, $PLC_{BCW}$, $PLC_{BCY}$ with O-(4-Nitrophenylphosphoryl)choline in aqueous media.

|  | $PLC_{BC}$ | $PLC_{BCW}$ | $PLC_{BCY}$ |
|---|---|---|---|
| $K_m$ (mM) | 39.5 | 14.8 | 17.4 |
| $k_{cat}$ (s$^{-1}$) | 3.90 | 5.44 | 4.86 |
| $k_{cat}/K_m$ (s$^{-1}$ M$^{-1}$) | 98.76 | 366.50 | 279.29 |

Kinetic Comparison of $PLC_{BC}$, $PLC_{BCW}$ and $PLC_{BCY}$ in Oil.

In order to compare the activity of wild type and mutant enzymes in oil, 3 ml of crude soybean oil containing 1000 ppm phosphate was homogenized (1 min using Ultra-Turrax T8 Homogenizer, IKA) with 22.5 µg of PLC in 90 µl of buffer HEPES 15 mM pH7, 1 mM ZnCl2, 10% glycerol. Each tube was incubated at 55° C. with constant agitation (VP 710 magnetic tumble stirrer, VP-Scientific). At different time points (5-10-20-40-60120 min) the oil was homogenized and 200 µl of the homogenized oil were mixed with 200 µl of 2M Tris-HCl pH 8 to stop the PLC reaction. Then, 800 µl of water was added, incubated for 1 h at 37° C. with constant agitation and centrifuged 5 min at 14000 g. 45 µl of the aqueous phase were recovered and treated with 0.3 U of calf intestinal phosphatase (Promega, Wis., USA) for 1 h at 37° C. following to the manufacturer instructions. Finally, inorganic phosphate was determined according to the method of Sumner (Sumner, J. B., Science 1944 196: 413). Briefly, a 500 µl sample, containing 0.025 to 0.25 µmol of inorganic phosphate in 5% TCA was mixed with 500 µl of color reagent (4% FeSO4, 1% (NH4)6MoO24.H2O, 3.2% H2SO4). Spectrophotometric readings were made at 700 nm, and the micromoles of inorganic phosphate in the sample were calculated from a standard curve.

Figure 3:
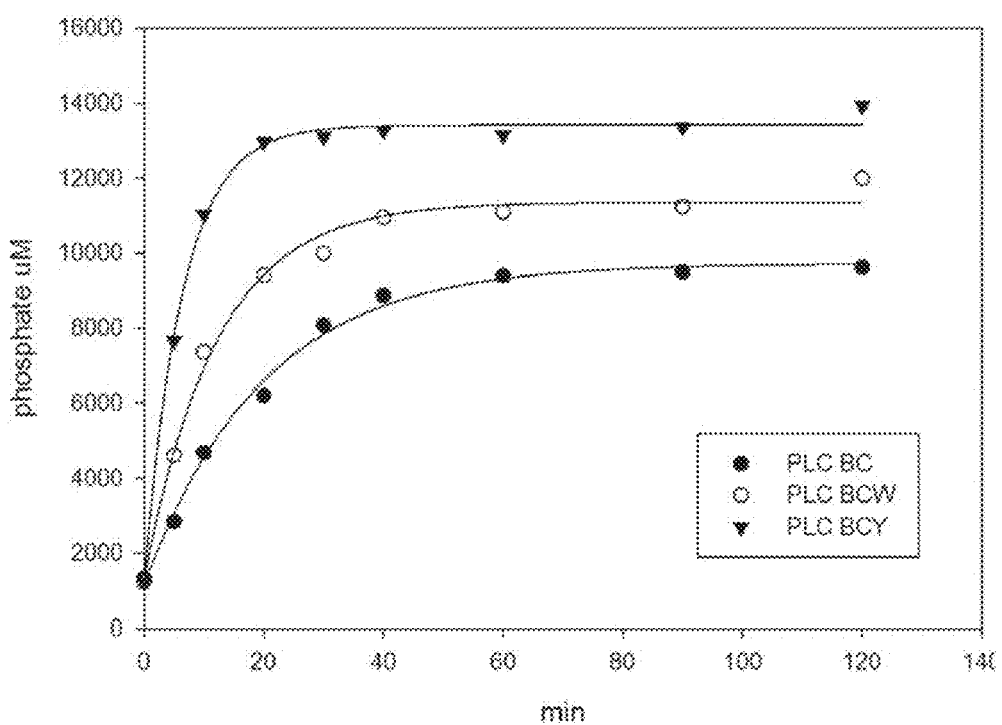
Figure 4:
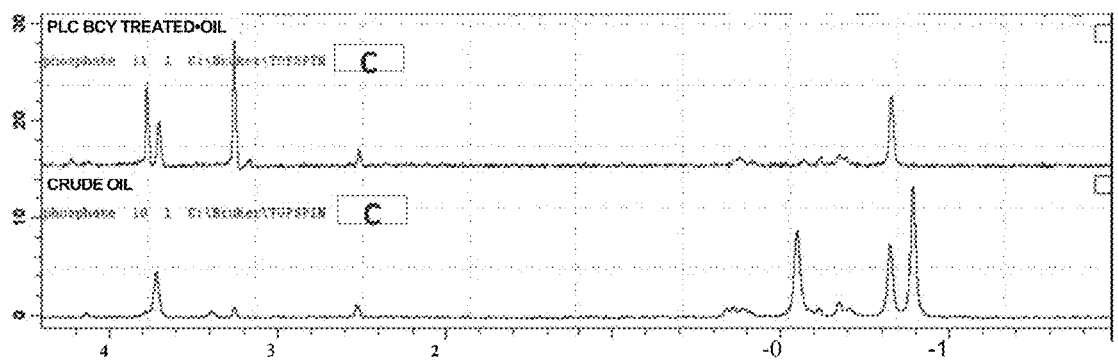

The results shown in FIG. 3 and Table 2 demonstrate that both mutant enzymes display a higher activity in oil than that of the wild type. Surprisingly and differing to the data obtained in aqueous environment, the $PLC_{BCY}$ enzyme shows superior catalytic properties in oil, indicating that the activity in aqueous environment cannot predict the efficiency of the mutant enzymes for the enzymatic degumming of oils.

TABLE 2

Kinetic parameters of $PLC_{BC}$, $PLC_{BCW}$, $PLC_{BCY}$ in crude oil

|  | $PLC_{BC}$ | $PLC_{BCW}$ | $PLC_{BCY}$ |
|---|---|---|---|
| $k_{cat}/K_m$ (s$^{-1}$M$^{-1}$) | 352.20 | 575.12 | 1094.34 |

Enzymatic Oil Degumming

Oil degumming experiments were performed using 200 g of crude soybean oil (1000 ppm phosphate), 3% H2O and 2.16 mg of the different PLCs obtained. The oil was emulsified with water using a Ultra-Turrax T 50 Homogenizer (1KA) for 1 min, and the containers incubated with continuous stirring with a magnetic stirrer at 55° C. for 2 h. Finally, the enzyme was heat-nactivated at 85° C. for 20 min and the oil centrifuged at 3000 g for 10 min to remove the remaining gums.1,2-diacylglicerol (1,2 DAG) content determination was performed according to AOCS Cd 11d-96: 2009. The results shown in Table 3 demonstrate the superior efficiency of the mutant enzymes for the oil degumming process. As expected from the kinetic analysis of the mutant enzymes in oil, the $PLC_{BCY}$ enzyme exhibits the highest catalytic efficiency.

TABLE 3

Oil degumming using $PLC_{BC}$, $PLC_{BCW}$, $PLC_{BCY}$

|  | 1,2 DAG (%) | Δ1,2DAG (%) |
|---|---|---|
| water | 0.35 | 0 |
| $PLC_{BC}$ | 1.14 | 0.79 |
| $PLC_{BCW}$ | 1.4 | 1.05 |
| $PLC_{BCY}$ | 1.53 | 1.18 |

$PLC_{BCY\ 134A}$ is protein SEQ ID NO: 5 with amino acid 134 changed to Ala. Oil degumming experiment was performed with $PLC_{BCY}$ and $PLC_{BCY}$ 134A and samples were taken at different time points and analyzed for 1.2 DAG content. We found a significant improvement in kinetic parameters when this amino acid is specifically changed to Ala.

TABLE 4

Oil degumming using $PLC_{BCY}$ and $PLC_{BCY\ 134A}$
Δ1,2DAG (%)

| min | PLC BCY | PLC BCY 134A |
|---|---|---|
| 20 | 0.83 | 1.08 |
| 40 | 0.91 | 1.07 |
| 60 | 1.01 | 1.19 |
| 140 | 1.21 | 1.20 |

NMR Analysis of Crude and $PLC_{BCY}$ Treated Oil.

Oil degumming experiments were performed as described above using $PLC_{BCY}$ for 2 hs at 55° C. Treated oil was emulsified using a Ultra-Turrax T 50 Homogenizer (IKA) for 1 min before taking 300 mg samples for further analysis. Oil samples were extracted with 900 µl of NMR solution (100 mM Tris-HCl pH 10.5, 50 mM EDTA, 2.5% sodium deoxycholate) during 1 h at 37° C. with constant agitation. Finally the resulting aqueous phase was extracted with 600 µl hexane and analyzed by NMR. NMR spectra were acquired using a Bruker DRX 600 equipment and samples of phosphatidylcholine, phosphatidylethanolamine, phosphatidic acid and phosphatidylinositol were run as standards.

What is claimed is:

1. A composition comprising:
an isolated phospholipase C enzyme comprising an amino acid sequence that is at least 98% identical to the amino acid sequence of SEQ ID NO:1, wherein the amino acid residue at position 66 is a Trp (W) or a Tyr (Y); and a vegetable oil.

2. The composition of claim 1, wherein said vegetable oil is selected from the group consisting of soybean, rapeseed, sunflower seed, rice bran, sesame, palm or peanut oil.

3. The composition of claim 1, wherein the amino acid residues at positions 63, 131 and 134 of said isolated phospholipase C enzyme are not Asn (N).

4. The composition of claim 3, wherein the amino acid residues at positions 63, 131 and 134 of said isolated phospholipase C enzyme are independently selected from a Ser (S) and an Asp (D).

5. The composition of claim 4, wherein the amino acid residues at positions 63 is an Asp (D), the amino acid residue at position 131 is a Ser (S), and the amino acid residue at position 134 is an Asp (D).

6. An isolated phospholipase C enzyme comprising an amino acid sequence that is at least 98% identical to the amino acid sequence of SEQ ID NO:1, wherein:
the amino acid residue at position 66 is a Trp (W) or Tyr (Y); and
the amino acid residues at positions 63, 131 and 134 are not Asn (N).

7. The isolated phospholipase C enzyme of claim 6, wherein the amino acid residues at positions 63, 131 and 134 are independently selected from a Ser (S) and an Asp (D).

8. The isolated phospholipase C enzyme of claim 6, wherein the amino acid residues at position 63 is a Asp (D), the amino acid residue at position 131 is a Ser (S) and the amino acid residue at position 134 is an Asp (D).

9. The isolated phospholipase C enzyme of claim 6, wherein said isolated polypeptide sequence comprises the amino acid sequence of SEQ ID NO:3 or SEQ ID NO:5.

10. The composition of claim 3, wherein the amino acid residue at position 63 is an Asp (D), the amino acid residue at position 131 is a Ser (S), and the amino acid residue at position 134 is an Ala (A).

11. The composition of claim 1, wherein said isolated polypeptide sequence comprises the amino acid sequence of SEQ ID NO:3.

12. The composition of claim 1, wherein said isolated polypeptide sequence comprises the amino acid sequence of SEQ ID NO:5.

13. The isolated phospholipase C enzyme of claim 6, wherein the amino acid residue at position 63 is an Asp (D), the amino acid residue at position 131 is a Ser (S), and the amino acid residue at position 134 is an Ala (A).

14. The isolated phospholipase C enzyme of claim 6, wherein said isolated polypeptide sequence comprises the amino acid sequence of SEQ ID NO:3.

15. The isolated phospholipase C enzyme of claim 6, wherein said isolated polypeptide sequence comprises the amino acid sequence of SEQ ID NO:5.

\* \* \* \* \*